US006946451B2

(12) United States Patent
Takada et al.

(10) Patent No.: US 6,946,451 B2
(45) Date of Patent: Sep. 20, 2005

(54) INSULIN SECRETION PROMOTER

(75) Inventors: Miho Takada, Tsukuba (JP); Toshikazu Kamiya, Tsukuba (JP); Tetsuo Endo, Stanford, CA (US); Satoshi Koizumi, Chiyoda-ku (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 87 days.

(21) Appl. No.: 10/356,564

(22) Filed: Feb. 3, 2003

(65) Prior Publication Data

US 2003/0181401 A1 Sep. 25, 2003

(30) Foreign Application Priority Data

Feb. 4, 2002 (JP) ........................................ 2002-027089

(51) Int. Cl.$^7$ ................... A61K 31/7016; A61K 31/702
(52) U.S. Cl. ............................. 514/53; 514/54; 514/61; 514/62
(58) Field of Search ............................. 514/53, 54, 61, 514/62

(56) References Cited

U.S. PATENT DOCUMENTS

| | | | |
|---|---|---|---|
| 4,122,188 A | * 10/1978 | Stacpoole | 514/557 |
| 4,705,687 A | * 11/1987 | Lau | 514/21 |
| 5,002,759 A | 3/1991 | Gaffar et al. | 424/49 |
| 5,164,374 A | 11/1992 | Rademacher et al. | 514/23 |
| 5,177,062 A | 1/1993 | Miyata et al. | 514/23 |
| 5,260,280 A | 11/1993 | Isoda et al. | 514/25 |
| 5,401,723 A | 3/1995 | Gaffar et al. | 514/21 |
| 5,468,734 A | 11/1995 | Seri et al. | 514/23 |
| 5,514,660 A | 5/1996 | Zopf et al. | 514/25 |
| 5,639,734 A | 6/1997 | Esko et al. | 514/25 |
| 6,083,934 A | 7/2000 | Prieto et al. | 514/61 |
| 6,596,707 B2 * | 7/2003 | Leach et al. | 514/61 |
| 6,777,397 B2 * | 8/2004 | Zehner et al. | 514/53 |

FOREIGN PATENT DOCUMENTS

| | | |
|---|---|---|
| DE | 197 01 382 | 7/1998 |
| EP | 0 313 533 | 10/1988 |
| EP | 0 473 108 | 3/1992 |
| WO | 99/56754 | 11/1999 |
| WO | 00/32205 | 6/2000 |
| WO | 01/43751 | 6/2001 |
| WO | 01/78748 | 10/2001 |

OTHER PUBLICATIONS

"Report of the Expert Committee on the Diagnosis and Classification of Diabetes Mellitus", *Diabetes Care*, vol. 20, No. 7 (1997), pp. 1183–1197.

Tritos, et al., "Syndromes of Severe Insulin Resistance", *Journal of Clinical Endocrinology and Metabolism*, vol. 83, No. 9 (1998), pp. 3025–3030.

Cevreska, et al., The Presence of Immunologically Reactive Insulin in Milk of Woman . . . , God. Zb. Med. Fak. Skopje, vol. 21 (1975), pp. 35–41.

Ukkonen, et al., "Treatment of acute otitis media with an antiadhesive oligosaccharide: a randomised, double–blind, placebo–controlled trial", *The Lancet*, vol. 356 (2000), pp. 1398–1402.

* cited by examiner

*Primary Examiner*—Leigh C. Maier
(74) *Attorney, Agent, or Firm*—Fitzpatrick, Cella, Harper & Scinto

(57) ABSTRACT

Provided are a method for promoting insulin secretion, a method for suppressing the elevation of a blood glucose level, a method for ameliorating diabetes mellitus, a method for promoting growth of an animal, and a method for increasing an insulin level in breast milk. These methods comprising administering at least one member selected from the group consisting of a di- or a higher saccharide containing galactose, a derivative thereof, a saccharide containing N-acetylneuraminic acid, and a derivative thereof, to a patient in need thereof or an animal.

18 Claims, No Drawings

INSULIN SECRETION PROMOTER

TECHNICAL FIELD

The present invention relates to a method for promoting insulin secretion, a method for suppressing the elevation of a blood glucose level and a method for ameliorating diabetes mellitus, a method for promoting growth of an animal, and a method for increasing an insulin level in breast milk. Additionally, the present invention relates to an agent, food, drink, or feed, or an additive for foods, drinks or feeds, which has an activity to increase insulin secretion, to suppress the elevation of a blood glucose level, to ameliorate diabetes mellitus, or to increase an insulin level in breast milk. Further, the present invention relates to a nutritious composition, a feed, and an additive for a nutritious composition or for feeds, which has an activity to promote growth of an animal.

BACKGROUND OF THE INVENTION

It has been known that diabetes mellitus is a risk factor of brain stroke and cardiac diseases. Additionally, diabetes mellitus also causes complications such as retinopathy, neuropathy, renal disorders and cataract. A survey executed by the Ministry of Health and Welfare, Japan reported in 1998 showed that 6.9 million individuals are strongly suspected of having diabetes mellitus, and that the total number of individuals with the possibility of having diabetes mellitus is estimated to be 13.7 million.

The survey of Japan Hospital Association reveals that 12.4% of persons in the hospital for a medical checkup in 1999 had abnormal glucose tolerance. The etiology of diabetes mellitus has not yet been elucidated completely. Diabetes mellitus is broadly classified as Type I diabetes mellitus with impairment of insulin secretion due to the damage of pancreatic beta-cells and Type II diabetes mellitus with reduced tissue sensitivity to insulin.

It has been said that Type II diabetes mellitus in the Japanese frequently involves relative shortage of insulin secretion. Therefore, agents for promoting insulin secretion have been used commonly.

It is thought that for preventing the onset of diabetes mellitus, reducing excess intake of animal fat, sugars and salt as well as increasing the intake of dietary fiber is effective. However, no regimen demonstrating a reliable effect has been established yet. As a method for therapeutically treating diabetes mellitus, insulin injection is accepted for Type I diabetes mellitus, while thiazolidine derivatives and biguanide as insulin resistance-ameliorating agents are used for Type II diabetes mellitus. Accepted foods for preventing or ameliorating diabetes mellitus include maltitol (a slightly digestible sugar), chitin and chitosan (dietary fiber), *Gymnema sylvestre* (a plant of the family Asclepiadaceae), and mulberry leaf (see Food Style 21, 2, No.5, 1998). As the mechanism under which such food prevent and ameliorate diabetes mellitus, it is suggested that some sweet substances are hardly absorbed from intestinal tract and so, increase of blood glucose level is reduced by inhibiting saccharide degrading enzymes.

Furthermore, known agents or foods for ameliorating high blood glucose level on the basis of the inhibition of α-glycosidase include monosaccharides such as L-arabinose, L-fucose, 2-deoxy-D-galactose, D-xylose, L-xylose, D-ribose, D-tagatose, D-ribulose, D-lyxose, and D-xylulose (U.S. Pat. No. 5,468,734).

It is known that insulin is a hormone secreted from the beta cells of pancreas and has activities to promote protein synthesis and glycogen synthesis in muscle and liver, to promote uptake and utilization of sugar in fat tissues, and to suppress lipolysis. It is also known that insulin promotes the growth of an infant. Furthermore, it is reported that the insulin level in breast milk increases as plasma insulin level increases due to post-meal or glucose loading (God. Zb. Med. Fak. Skopje., 21, 35–41, 1975).

It has been desired to develop a pharmaceutical agent, as well as a food or drink or an animal feed, which can effectively ameliorate, prevent or therapeutically treat diabetes mellitus via daily intake.

DISCLOSURE OF THE INVENTION

It is an object of the present invention to provide an insulin secretion promoter, an agent for suppressing the elevation of a blood glucose level, an agent for ameliorating diabetes mellitus, an agent for promoting growth of an animal or an agent for increasing an insulin level in breast milk. Additionally, it is an object of the present invention to provide a food or drink, a feed, an additive for foods, drinks or feeds, which has activities to promote insulin secretion, to suppress the elevation of a blood glucose level, to ameliorate diabetes mellitus, or to increase an insulin level in breast milk, as well as a nutritious composition, a feed, an additive for nutritious compositions, or for feeds, which has an activity to promote growth of an animal.

The present invention relates to the following aspects (1) to (42).

(1) A method for promoting insulin secretion, comprising administering at least one member selected from the group consisting of a di- or higher saccharide containing galactose, a derivative thereof, a saccharide containing N-acetylneuraminic acid, and a derivative thereof, to a patient in need thereof.

(2) The method for promoting insulin secretion according to claim 1, comprising administering the di- or higher saccharide containing galactose and additionally N-acetylglucosamine or glucose.

(3) The method for promoting insulin secretion according to claim 2, where the di- or higher saccharide containing galactose and additionally N-acetylglucosamine or glucose is a di- or higher saccharide containing N-acetyllactosamine or lactose.

(4) The method for promoting insulin secretion according to claim 1, comprising administering N-acetyllactosamine, lacto-N-neotetraose, globotriose, 2'-fucosyllactose, 3'-sialyllactose, 6'-sialyllactose, or N-acetylneuraminic acid.

(5) The method for promoting insulin secretion according to any of claims 1 to 4, where the patient is a human.

(6) The method for promoting insulin secretion according to any of (1) to (4), where the patient is an animal.

(7) The method for promoting insulin secretion according to (6), where the animal is a domestic mammal, domestic fowl, or cultivated fish.

(8) The method for promoting insulin secretion according to any of (1) to (4), where the administration is carried out orally or by injection.

(9) A method for suppressing the elevation of a blood glucose level, comprising administering at least one member selected from the group consisting of a di- or higher saccharide containing galactose, a derivative thereof, a saccharide containing N-acetylneuraminic acid, and a derivative thereof, to a patient in need thereof.

(10) The method for suppressing the elevation of a blood glucose level according to (9), comprising administering the di- or higher saccharide containing galactose and additionally N-acetylglucosamine or glucose.

(11) The method for suppressing the elevation of a blood glucose level according to (10), where the di- or higher saccharide containing galactose and additionally N-acetylglucosamine or glucose is a di- or higher saccharide containing N-acetyllactosamine or lactose.
(12) The method for suppressing the elevation of a blood glucose level according to (9), comprising administering N-acetyllactosamine, lacto-N-neotetraose, globotriose, 2'-fucosyllactose, 3'-sialyllactose, 6'-sialyllactose, or N-acetylneuraminic acid.
(13) The method for suppressing the elevation of a blood glucose level according to any of (9) to (12), where the patient is a human.
(14) The method for suppressing the elevation of a blood glucose level according to any of (9) to (12), where the patient is an animal.
(15) The method for suppressing the elevation of a blood glucose level according to (14), where the animal is a domestic mammal, domestic fowl, or cultivated fish.
(16) The method for suppressing the elevation of a blood glucose level according to any of (9) to (12), where the administration is carried out orally or by injection.
(17) A method for ameliorating diabetes mellitus, comprising administering at least one member selected from the group consisting of a di- or higher saccharide containing galactose, a derivative thereof, a saccharide containing N-acetylneuraminic acid, and a derivative thereof, to a patient in need thereof.
(18) The method for ameliorating diabetes mellitus according to (17), comprising administering the di- or higher saccharide containing galactose and additionally N-acetylglucosamine or glucose.
(19) The method for ameliorating- diabetes mellitus according to (18), where the di- or higher saccharide containing galactose and additionally N-acetylglucosamine or glucose is a di- or higher saccharide containing N-acetyllactosamine or lactose.
(20) The method for ameliorating diabetes mellitus according to (17), comprising administering N-acetyllactosamine, lacto-N-neotetraose, globotriose, 2'-fucosyllactose, 3'-sialyllactose, 6'-sialyllactose, or N-acetylneuraminic acid.
(21) The method for ameliorating diabetes mellitus according to any of (17) to (20), where the patient is a human.
(22) The method for ameliorating diabetes mellitus according to any of (17) to (20), where the patient is an animal.
(23) The method for ameliorating diabetes mellitus according to (22), where the animal is a domestic mammal, domestic fowl, or cultivated fish.
(24) The method for ameliorating diabetes mellitus according to any of (17) to (20), where the administration is carried out orally or by injection.
(25) A method for promoting growth of an animal, comprising administering at least one member selected from the group consisting of a di- or a higher saccharide containing galactose, a derivative thereof, a saccharide containing N-acetylneuraminic acid, and a derivative thereof, to an animal.
(26) The method for promoting growth of an animal according to (25), comprising administering the di- or higher saccharide containing galactose and additionally N-acetylglucosamine or glucose.
(27) The method for promoting growth of an animal according to (26), where the di- or higher saccharide containing galactose and additionally N-acetylglucosamine or glucose is a di- or higher saccharide containing N-acetyllactosamine or lactose.
(28) The method for promoting growth of an animal according to (25), comprising administering N-acetyllactosamine, lacto-N-neotetraose, globotriose, 2'-fucosyllactose, 3'-sialyllactose, 6'-sialyllactose, or N-acetylneuraminic acid.
(29) The method for promoting growth of an animal according to any of (25) to (28), where the animal is a human.
(30) The method for promoting growth of an animal according to (29), where the human is an human infant.
(31) The method for promoting growth of an animal according to any of (25) to (28), where the animal is a domestic mammal, domestic fowl or cultivated fish.
(32) The method for promoting growth of an animal according to any of (25) to (28), where the administration is carried out orally or by injection.
(33) method for increasing an insulin level in breast milk, comprising administering at least one member selected from the group consisting of a di- or higher saccharide containing galactose, a derivative thereof, a saccharide containing N-acetylneuraminic acid, and a derivative thereof, to a mammal.
(34) The method for increasing an insulin level in breast milk according to (33), comprising administering the di-or higher saccharide containing galactose and additionally N-acetylglucosamine or glucose.
(35) The method for increasing an insulin level in breast milk according to (34), where the di- or higher saccharide containing galactose and additionally N-acetylglucosamine or glucose is a di- or higher saccharide containing N-acetyllactosamine or lactose.
(36) The method for increasing an insulin level in breast milk according to (33), comprising administering N-acetyllactosamine, lacto-N-neotetraose, globotriose, 2'-fucosyllactose, 3'-sialyllactose, 6'-sialyllactose, or N-acetylneuraminic acid.
(37) The method for increasing an insulin level in breast milk according to any of (33) to (36), where the mammal is a human. (38) The method for increasing an insulin level in breast milk according to any of (33) to (36), where the mammal is a domestic mammal.
(39) The method for increasing an insulin level in breast milk according to any of (33) to (36), where the administration is carried out orally or by injection.
(40) A method for promoting growth of an animal, comprosong feeding breast milk from a mammal administered with at least one member selected from the group consisting of a di- or higher saccharide containing galactose, a derivative thereof, a saccharide containing N-acetylneuraminic acid, and a derivative thereof.
(41) The method according to (40), where the mammal is a human.
(42) The method according to (40), where the mammal is a domestic mammal.

In accordance with the present invention, the insulin secretion promoter, the agent for suppressing the elevation of the blood glucose level, the agent for ameliorating diabetes mellitus, the agent for promoting growth of an animal, or the agent for increasing an insulin level in breast milk comprises at least one member selected from the group consisting of a di- or higher saccharide containing galactose, a derivative thereof, a saccharide containing N-acetylneuraminic acid, and a derivative thereof as an active ingredient (sometimes hereinafter referred to as "active ingredient").

As the di- or higher saccharide containing galactose, any galactose-containing di- or higher saccharide may be used satisfactorily. The saccharide is preferably a di- or higher saccharide containing galactose as well as N-acetylglucosamine or glucose, even more preferably a di- or higher saccharide containing N-acetyllactosamine or lactose.

The di- or higher saccharide containing galactose as well as N-acetylglucosamine or glucose includes, for example, N-acetyllactosamine, globotriose, 2'-fucosyllactose, 3'-sialyllactose, 6'-sialyllactose, 2'-fucosyl-N-acetyllactosamine, 3'-sialyl-N-acetyllactosamine, 6'-sialyl-N-acetyllactosamine, lacto-N-tetraose, lacto-N-neotetraose, 2'-fucosyllacto-N-tetraose, 2'-fucosyllacto-N-neotetraose, 3'-sialyllacto-N-tetraose, 3'-sialyllacto-N-neotetraose, 6'-sialyllacto-N-tetraose, and 6'-sialyllacto-N-neotetraose.

The di- or higher saccharide containing N-acetyllactosamine includes, for example, N-acetyllactosamine, 2'-fucosyl-N-acetyllactosamine, 3'-sialyl-N-acetyllactosamine, 6'-sialyl-N-acetyllactosamine, lacto-N-neotetraose, 2'-fucosyllacto-N-neotetraose, 3'-sialyllacto-N-neotetraose, and 6'-sialyllacto-N-tetraose, and preferably includes N-acetyllactosamine and lacto-N-neotetraose.

The di- or higher saccharide containing lactose includes, for example, globotriose, 2'-fucosyllactose, 3'-sialyllactose, 6'-sialyllactose, lacto-N-tetraose, lacto-N-neotetraose, 2'-fucosyllacto-N-tetraose, 2'-fucosyllacto-N-neotetraose, 3'-sialyllacto-N-tetraose, 3'-sialyllacto-N-neotetraose, 6'-sialyllacto-N-tetraose, and 6'-sialyllacto-N-neotetraose, and preferably includes globotriose, 2'-fucosyllactose, 3'-sialyllactose, 6'-sialyllactose, and lacto-N-neotetraose.

The saccharide containing N-acetylneuraminic acid includes, for example, N-acetylneuraminic acid, 3'-sialyllactose, 6'-sialyllactose, 3'-sialyl-N-acetyllactosamine, 6'-sialyl-N-acetyllactosamine, 3'-sialyllacto-N-tetraose, 6'-sialyllacto-N-tetraose, 3'-sialyllacto-N-neotetraose, and 6'-sialyllacto-N-neotetraose, and preferably includes N-acetylneuraminic acid, 3'-sialyllactose, and 6'-sialyllactose.

The saccharides can be obtained either by chemical synthetic methods, or by isolation and purification from naturally occurring substances containing the saccharides. Furthermore, the saccharides can be obtained by purchasing commercially available products.

Chemical syntheses of saccharides are described in "Carbohydrates in Chemistry and Biology" (B. Ernst et al., ed., Willey-VCH, 2000). Such methods are all well known to those of ordinary skill, but representative methods are enumerated for individual saccharides.

Methods for producing saccharides containing galactose are described in WO98/12343.Methods for producing saccharides containing N-acetylneuraminic acid are described in U.S. Pat. No. 5,374,541.Methods for producing saccharides containing fucose are described in WO93/08205.

Methods for producing N-acetyllactosamine are described in WO98/12343 and Carbohydr. Res., 316, 179 (1999); methods for producing lacto-N-neotetraose are described in WO98/12343; methods for producing globotriose are described in WO98/12343 and Nat. Biotechnol., 16, 847 (1998); methods for producing 3'-sialyllactose are described in Appl. Microbiol. Biotechnol., 53, 257 (2000); methods for producing 6'-sialyllactose are described in Appl. Microbiol. Biotechnol., 53, 257 (2000); methods for producing 2'-fucosyllactose are described in J. Ind. Microbiol. Biotechnol., 25, 213 (2000); methods for producing N-acetylneuraminic acid are described in U.S. Pat. No. 5,665,574, Carbohydr. Res., 306, 575 (1998), and EP 1,081,230.

Methods for isolating saccharides from naturally occurring substances are also well-known in this art and include methods using columns, see The Japanese Biochemical Sosceity, ed., New Biochemical Experimental Series No. 3, Saccharide I, (Tokyo Kagaku Dojin), 1990.Preferable method utilizes gel filtration column chromatography and high-performance liquid chromatography.

All of globotriose, N-acetyllactosamine, lacto-N-neotetraose, 3'-sialyllactose, 6'-sialyllactose, 2'-fucosyllactose, and N-acetylneuraminic acid can be purchased commercially, for instance from Sigma-Aldrich.

The insulin secretion promoter, the agent for suppressing the elevation of a blood glucose level, the agent for ameliorating diabetes mellitus, the agent for promoting growth of an animal, or the agent for increasing an insulin level in breast milk comprising the active ingredient according to the present invention may also contain one or more pharmacologically or comestible acceptable carriers and other effective components for therapeutic treatment if necessary.

The pharmaceutical preparation of the present invention can be produced by mixing the active ingredient, namely at least one member selected from the group consisting of a di- or higher saccharide containing galactose, a derivative thereof, a saccharide containing N-acetylneuraminic acid, and a derivative thereof, with a carrier, if necessary, by a method well known in the technical field of pharmaceutics.

As the dosage regimen of the pharmaceutical preparation, an effective dosage regimen for therapeutic treatment is readily determined. Such regimen includes oral administration or parenteral administration such as intravenous administration, intraperitoneal administration, or subcutaneous administration. Among them, intravenous administration or oral administration is preferred.

The dosage form for administration includes, for example, tablets, powders, granules, pills, suspensions, emulsions, infusions, capsules, syrups, injections, liquids, elixirs, extracts, tincture and fluid extracts.

Liquid preparations suitable for oral administration, for example syrups can be prepared, using water, conventional saccharides such as sucrose, sorbitol and fructose, glycols such as polyethylene glycol and propylene glycol, oils such as sesame seed oil, olive oil and soybean oil, antiseptics such as p-hydroxybenzoate ester, preservatives such as p-hydroxybenzoate derivatives, for example p-hydroxybenzoate methyl and sodium benzoate, and other materials such as flavors, for example strawberry flavor and peppermint.

Further, preparations suitable for oral administration, for example tablets, powders and granules can be produced, using conventional saccharides such as lactose, sucrose, glucose, sucrose, mannitol, and sorbitol, starch such as potato, wheat and corn, inorganic materials such as calcium carbonate, calcium sulfate, sodium hydrogen carbonate, and sodium chloride, plant powders such as crystal cellulose, licorice powder and gentian powder, excipients such as pinedex, disintegrators such as starch, agar, gelatin powder, crystal cellulose, carmellose sodium, carmellose calcium, calcium carbonate, sodium hydrogen carbonate and sodium alginate, lubricants such as magnesium stearate, talc, hydrogenated vegetable oils, macrogol, and silicone oil, binders such as polyvinyl alcohol, hydroxypropyl cellulose, methyl cellulose, ethyl cellulose, carmellose, gelatin, and starch glue fluid, surfactants such as fatty acid ester, and plasticizers such as glycerin.

Injections suitable for parenteral administration are sterile aqueous agents comprising an active ingredient, which are preferably isotonic to the blood of an acceptor. In case of injections, for example, solutions for injection are prepared, using carriers such as salt solutions, glucose solutions or mixtures of salt solutions and glucose solutions.

Even in these parenteral agents, the antiseptics, preservatives and surfactants, etc. can additionally be used.

The dosage dose and number of the insulin secretion promoter, the agent for suppressing the elevation of glucose level, the agent for ameliorating diabetes mellitus, the agent for promoting growth of an animal or the agent for increasing an insulin level in breast milk in accordance with the present invention vary, depending on the method of administration, the age and body weight of a patient, the nature of the symptom to be therapeutically treated, and the severity thereof. Nevertheless, in case of ordinary oral administration, the dose is generally 1 mg to 50 g per adult per day, preferably 5 mg to 20 g per adult per day once daily or in several portions daily. In case of parenteral dosing such as intravenous dosing, the dose is 0.1 mg to 50 g per adult per day, preferably 1 mg to 10 g per adult per day once daily or in several portions daily. In case of dosing to animals, further, the dose varies depending on the age and species of an animal and the nature or severity of the symptom thereof. Without any specific limitation, the dose for animals is 0.1 mg to 10 g per 1 kg body weight, preferably 1 mg to 1 g per 1 kg body weight once daily or in several portions daily. In case of parenteral dosing for animals such as intravenous dosing, the dose is 0.01 mg to 10 g per 1 kg body weight, preferably 1 mg to 1 g per 1 kg body weight once daily or in several portions daily. However, these doses and the number of dosages vary depending on the individual conditions.

Furthermore, the present invention relates to a food, drink or feed with an activity to promote insulin secretion, an activity to suppress the elevation of a blood glucose level, an activity to ameliorate diabetes mellitus, an activity to promote growth of an animal or an activity to increase an insulin level in breast milk. Such food drink or feed can be produced by a general method for producing foods and drinks or feeds, including, adding the active ingredient, namely at least one member selected from the group consisting of a di- or a higher saccharide containing galactose, a derivative thereof, a saccharide containing N-acetylneuraminic acid, and a derivative thereof, to a raw or cooked material of the food, drink or feed.

The food, drink or feed in accordance with the present invention can be molded and granulated in the same manner as generally used for foods, drinks or feeds.

The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

The food, drink or feed according to the present invention includes foods, drinks or feeds comprising the active ingredient, namely at least one member selected from the group consisting of a di- or higher saccharide containing galactose, a derivative thereof, a saccharide containing N-acetylneuraminic acid, or a derivative thereof. This food, drink or feed includes any food, drink or feed. Moreover, the active ingredient, namely the di- or higher saccharide containing galactose, or a derivative thereof, or a saccharide containing N-acetylneuraminic acid, or a derivative thereof, in the food, drink or feed is not specifically limited to any concentration as long as the resulting food, drink or feed can exert an activity to promote insulin secretion, an activity to suppress the elevation of a blood glucose level, an activity to ameliorate diabetes mellitus, an activity to promote growth of an animal, or an activity to increase an insulin level in breast milk. The concentration of the active ingredient is preferably 0.001 to 100% by weight, more preferably 0.01 to 100% by weight and most preferably 0.1 to 100% by weight of the food, drink or feed comprising such active ingredient.

Specific foods or drinks, to which the active ingredient is added, include, for example, juices, refreshing drinks, soups, teas, sour milk beverages, dairy products such as fermented milks, ices, butter, cheese, yogurt, processed milk and skim milk, meat products such as ham, sausage, and hamburger, fish meat cake products, egg products such as seasoned egg rolls and egg curd, confectioneries such as cookie, jelly, snacks, and chewing gum, breads, noodles, pickles, smoked products, dried fishes, soy sauce-seasoned boiled foods (Japanese tsukudani) and seasonings.

The form of the food or drink includes, for example, powder foods, sheet-like foods, bottled foods, canned foods, retort foods, capsule foods, tablet foods and fluid foods.

The food or drink with an activity to promote insulin secretion and the food or drink with an activity to promote growth of an animal, which are to be ingested by infants, are preferably nutritious compositions for infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion.

The nutritious composition for infants in accordance with the present invention is principally composed of protein, lipid, saccharide, vitamins and/or minerals. In the nutritious composition, the active ingredient, namely at least one member selected from the group consisting of a di- or higher saccharide containing galactose, a derivative thereof, a saccharide containing N-acetylneuraminic acid, and a derivative thereof, is blended with these components. The protein composing the nutritious composition for infants includes milk proteins such as skim milk, casein, cheese whey, whey protein concentrate, and whey protein isolates, and their fractions such as αs-casein, β-casein, α-lactoalbumin, and β-lactoglobulin. Further, egg protein such as egg yolk protein, egg white protein, and ovalbumin, or soybean protein such as defatted soybean protein, separated soybean protein, and concentrated soybean protein can be used. Other than these, proteins such as wheat gluten, fish meat protein, cattle meat protein and collagen may also be used satisfactorily. Further, fractions of these proteins, peptides from the acid or enzyme treatment thereof, or free amino acids may be used satisfactorily as well. The free amino acids can serve as nitrogen sources and can additionally be used to give specific physiological actions. Such free amino acids include, for example, taurine, arginine, cysteine, cystine and glutamine. The amount of such proteins, peptides or free amino acids to be blended is 5 to 30% by weight per the total solid in a nutritious composition for infants. The lipid includes animal fats and oils such as milk fat, lard, beef fat and fish oil, vegetable oils such as soybean oil, rapeseed oil, corn oil, coconut oil, palm oil, palm kernel oil, safflower oil, perilla oil, linseed oil, evening primrose oil, medium chain fatty acid triglyceride, and cotton seed oil, bacterially generated fats and oils, and fractionated oils thereof, hydrogenated oils thereof, and ester exchange oils thereof. The amount of lipid to be blended varies depending on the use. Preferably, the amount is 40% by weight or less per the total solid in the nutritious composition for infants. The saccharide includes, for example, one or more of starch, soluble polysaccharides, dextrin, monosaccharides such as sucrose, lactose, maltose, glucose, and fructose, 6'-galactosyllactose, 4'-galactosyllactose, fructooligosaccharide, lactulose, and other oligosaccharides. The total amount of such saccharide is preferably 40 to 80% by weight to the total solid in the nutritious composition. Further, artificial sweeteners such as aspartame may be used satisfactorily. The amount of an artificial sweetener is appropriately 0.05 to 1.0% by weight per the total solid in the nutritious composition.

The vitamins and minerals for use in the nutritious composition for infants in accordance with the present invention include, but are not limited to, the vitamins and minerals described in "The CODEX standards for specific-use foods including foods for infants and related hygienic working rules, CAC/VOL/IX-The first edition and Supplements 1, 2, 3 and 4" (as issued by The Japanese National Committee of International Dairy Federation, 1993), "The 1993 Manual of Designated Food Additives (the revised 31st edition)" (Shokuhin To Kagaku, 1993) and "Manual of food additives under report rule and natural food materials (12th edition)" (Shokuhin To Kagaku, 1992), as long as such vitamins and minerals can be administered to infants. The vitamins and minerals typically include lycopene as an essential component and additionally include, for example, vitamins such as vitamin A, vitamin B group, vitamins C, D, and E and vitamin K group, folic acid, pantothenic acid, nicotinamide, carnitine, choline, inositol and biotin. Such vitamins are preferably from 10 mg to 5 g % by weight per the total solid in the nutritious composition for infants. Further, the minerals include calcium, magnesium, potassium, sodium, iron, copper, zinc, phosphorus, chlorine, manganese, selenium and iodine. Such minerals are preferably from 1 mg to 5 g % by weight per the total solid in the nutritious composition for infants. Other than those components described above, the nutritious composition for infants of the present invention may be blended with any component desirably blended in nutritious compositions, for example, dietary fiber, nucleotides, nucleic acids, flavors, and colorants.

The food or drink of the present invention can be used as a health food or drink or a functional food or drink to promote insulin secretion, suppress the elevation of a blood glucose level, ameliorate diabetes mellitus, promote growth of an animal or increase an insulin level in breast milk. Breast milk produced during increased insulin has a higher activity to promote growth of an animal than breast milk generally does.

When the food or drink according to the present invention is ingested, the amount to be ingested is not specifically limited. The amount thereof ingested is generally 0.1 to 50 g, preferably 0.5 g to 20 g daily, based on the total amount of active ingredient. The food or drink is continuously ingested at this amount for a period from a single day up to 5 years, preferably from 2 weeks to one year. Herein, the amount ingested can be adjusted to an appropriate range depending on the severity of the symptom of the individual ingesting the food or drink, the age and body weight thereof, and the like.

The feed of the present invention may be any feed comprising the active ingredient, namely at least one member selected from the group consisting of a di- or higher saccharide containing galactose, a derivative thereof, a saccharide containing N-acetylneuraminic acid and a derivative thereof, for mammals, birds, reptiles, amphibians, and fishes. The feed includes, for example, pet feeds for dogs, cats and rats, cattle feeds for cows and pigs, chicken feeds for chicken and turkeys, and fish cultivation feeds for porgy and yellowtail.

The feed can be produced by appropriately blending the active ingredient of the present invention in a raw feed material including, for example, cereals, brans, oil-seed meals, animal-derived raw feed materials, other raw feed materials and purified products.

The cereals include, for example, milo, wheat, barley, oats, rye, brown rice, buckwheat, foxtailmillet, Chinesemillet, Deccan grass, corn, and soybean.

The brans include, for example, rice bran, defatted rice bran, bran, lowest-grade flour, wheat germ, barley bran, screening pellet, corn bran, and corn germ.

The oil-seed meals include, for example, soybean meal, soybean powder, linseed meal, cottonseed meal, peanut meal, safflower meal, coconut meal, palm meal, sesame meal, sunflower meal, rapeseed meal, kapok seed meal and mustard meal.

The animal-derived raw feed materials include, for example, fish powders such as Hokuyo Meal, import meal, whole meal, and coast meal, fish soluble, meat powder, meat and bone powder, blood powder, decomposed hair, bone powder, byproducts from butchery, feather meal, silkworm pupa, skim milk, casein, dry whey and krill.

Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chlorella.

The purified products include, for example, proteins such as casein and albumin, amino acids, starch, cellulose, saccharides such as sucrose and glucose, minerals and vitamins.

In case of providing to animals the feed according to the present invention, the amount of the feed to be ingested is not specifically limited but is 0.1 mg to 50 g per 1 kg body weight per day, preferably 0.5 mg to 20 g per 1 kg body weight per day, based on the amount of the active ingredient. The feed is continuously ingested at this amount for a period from a single day up to 5 years, preferably from 2 weeks to one year. Again, the amount ingested can be adjusted to an appropriate range depending on the species, age and body weight of the animal ingesting the feed, and the like.

Furthermore, the present invention relates to an additive for foods, drinks and feeds, to achieve an activity to promote insulin secretion, an activity to suppress the elevation of a blood glucose level, an activity to ameliorate diabetes mellitus, an activity to promote growth of an animal, or an activity to increase an insulin level in breast milk. The additive for foods or drinks includes the additive for nutritious compositions for infants.

The additive for foods, drinks or feeds has a disaccharide or a higher saccharide containing galactose, a derivative thereof, a saccharide containing N-acetylneuraminic acid, or a derivative thereof as the effective ingredient, can be produced by a general method for producing additives for foods, drinks or feeds. If necessary, additives for general use in foods, drinks or feeds, for example, additives described in Food Additive Handbook (The Japan Food Additives Association; issued on Jan. 6, 1997) may be added satisfactorily, including sweeteners, colorants, preservatives, thickeners and stabilizers, anti-oxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers mentioned previously for pharmaceutical tablets may be added satisfactorily.

The additives include the following additives.

The sweeteners include aspartame, licorice, stevia, xylose and rakanka (*Momordica grosvenori* fruit). The colorants include carotenoid and turmeric oleoresin, flavonoid, caramel color, Shikon (*Lithospermum erythrorhizon* root) color, spirulina color, chlorophyll, purple sweet potato color, purple yam color, perilla color, and blueberry color.

The preservatives include, for example, sodium sulfite, benzoates, udo (*Aralia cordata*) extract, benzoin (*Styrax benzoin*) extract, capillary wormwood (*Artemisia capillaris*) extract, sorbates, and propionates. The thickeners and stabilizers include, for example, gums such as gum arabic and xanthan gum, alginates, chitin, chitosan, *Aloe arborescens* extract, guar gum, hydroxypropyl cellulose, sodium casein, corn starch, carboxymethyl cellulose, gelatin, agar, dextrin, methyl cellulose, polyvinyl alcohol, microfiber cellulose, microcrystalline cellulose, seaweed cellulose, sodium polyacrylate, sodium polyphosphate, carrageenan, yeast cell wall, konjak (*Amorphophallus konjac*) root extract, nata de coco, and mannan.

The anti-oxidants include, for example, vitamin C group, sodium ethylenediaminetetraacetate, calcium ethylenediaminetetraacetate, erythorbic acid, oryzanol, catechin, quercetin, clove extract, enzyme-treated rutin, apple extract, sesame seed extract, dibutylhydroxytoluene, fennel extract, horseradish extract, water celery (*Oenanthe javanica*) extract, tea extract, tempeh extract, dokudami (*Houttuynia cordata*) extract, tocotrienol, tocopherols, rapeseed extract, coffee bean extract, sunflower seed extract, ferulic acid, butylhydroxyanisole, blueberry leaf extract, propolis extract, hego (*Cyathea fauriei*)-gingko leaf extract, hesperetin, pepper extract, garden balsam extract, gallic acid, Chinese bayberry extract, eucalyptus extract, and rosemary extract.

The color fixing agents include, for example, sodium nitrite. The bleaches include, for example, sodium sulfite.

The antiseptics include, for example, o-phenyl phenol.

The gum base includes, for example, acetylricinoleate methyl, urushi wax, ester gum, elemi resin, urucury wax, ozokerite, opopanax resin, kaurigum, carnauba wax, guaiac resin, gutta katiau, gutta hang kang, gutta percha, glycerin fatty acid ester, spermaceti wax, copaiba balsam, copal resin, rubber, rice bran wax, cane wax, shellac, jelutong, sucrose fatty acid ester, sorva, sorbitan fatty acid ester, talc, calcium carbonate, dammar resin, chicle, chilte, Tunu, depolymerized natural rubber, paraffin wax, fir balsam, propylene glycol fatty acid ester, powdered pulp, powdered rice hulls, jojoba oil, polyisobutylene, polybutene, microcrystalline wax, mastic gum, massaranduba chocolate, bees wax and calcium phosphate.

The bitters include, for example, iso-alpha-bitter acid, caffeine, kawaratake (*Coriolus versicolor*) extract, redbark cinchona extract, *Phellodendron* bark extract, gentian root extract, spice extracts, enzymatically modified naringin, Jamaica cassia extract, theobromine, naringin, cassia extract, absinth extract, isodonis extract, himematsutake (*Agaricus blazei*) extract, borapet, methylthioadenosine, Mannentake (*Ganoderma lucidum*) extract, olive tea, bitter orange (*Citrus aurantium*) extract, hop extract and wormwood extract.

The enzymes include, for example, amylase, trypsin, rennet and lactobacillus.

The brightening agents include, for example, urushi wax and japan wax. The acidifier include, for example, adipic acid, itaconic acid, citric acids, succinic acids, sodium acetate, tartaric acids, carbon dioxide, lactic acid, phytic acid, fumaric acid, malic acid and phosphoric acid. The seasonings include, for example, amino acids such as asparagine, aspartic acid, glutamic acid, glutamine, alanine, isoleucine, glycine, serine, cystine, tyrosine, leucine, and proline, nucleic acids such as sodium inosinate, sodium uridinate, sodium guanylate, sodium cytidylate, calcium ribonucleotide and sodium ribonucleotide, organic acids such as citric acid and succinic acid, potassium chloride, sodium chloride-decreased brine, crude potassium chloride, whey salt, tripotassium phosphate, dipotassium hydrogen phosphate, potassium dihydrogen phosphate, disodium hydrogen phosphate, sodium dihydrogen phosphate, trisodium phosphate and chlorella extract.

The enhancers include, for example, zinc salts, vitamin C group, various amino acids, 5-adenylic acid, iron chloride, hesperidin, various calcined calcium, various non-calcined calcium, dibenzoylthiamine, calcium hydroxide, calcium carbonate, thiamine hydrochloride salt, *Dunaliella* carotene, tocopherol, nicotinic acid, carrot carotene, palm oil carotene, calcium pantothenate, vitamin A, hydroxyproline, calcium dihydrogen pyrophosphate, ferrous pyrophosphate, ferric pyrophosphate, ferritin, heme iron, menaquinone, folic acid and riboflavine.

The agents for manufacture include, for example, processing auxiliaries such as acetone and ion exchange resin, fig leaf extract, rice straw ash extract, kaolin, glycerin fatty acid ester, mulberry extract, bone ash, perilla extract, ginger extract, various tannins, paffia extract, grape seed extract, and ethanol.

The flavors include, for example, vanilla essence and the spice extracts include, for example, capsicum extract.

These various additives can be added to the active ingredient, taking into consideration the mode of administration, in accordance with the present invention.

It is possible in humans or animals to promote insulin secretion, suppress the elevation of a blood glucose level, ameliorate diabetes mellitus, promote growth of an animal or increase an insulin level in breast milk, by dosing with the active ingredient. Additionally, the growth of an animal can be promoted by administration of breast milk containing the increased insulin to human or animal.

The present invention will now be described below with reference to the following examples. However, the examples do not limit the scope of the present invention.

EXAMPLE 1

Production of an Insulin Secretion Promoter Comprising 2'-fucosyllactose

An insulin secretion promoter of the following composition was produced by mixing the individual components together.

| | |
|---|---|
| 2'-Fucosyllactose | 49 g |
| Pinexex #3 (excipient; Matsutani Chemical Industry, Co., Ltd.) | 49 g |
| Ferric pyrophosphate (iron source) | 0.1 g |
| PhosCal EFC (calcium source; Nikko Fine Product, Co.) | 1 g |
| Vitamin mix (Merck Co.) | 1 g |

EXAMPLE 2
Production of an Insulin Secretion Promoter Comprising N-acetylneuraminic Acid An insulin secretion promoter of the following composition was produced by mixing the individual components together.

| | |
|---|---|
| N-Acetylneuraminic acid | 49 g |
| Pinedex #3 (excipient; Matsutani Chemical Industry, Co., Ltd.) | 49 g |
| Ferric pyrophosphate (iron source) | 0.1 g |
| PhosCal EFC (calcium source; Nikko Fine Product, Co.) | 1 g |
| Vitamin mix (Merck Co.) | 1 g |

EXAMPLE 3
Production of an Insulin Secretion Promoter Comprising 2'-fucosyllactose and N-acetylneuraminic Acid 2'-Fucosyllactose (10 g) and N-acetylneuraminic acid (10 g) were dispersed in 180 ml of water, to produce an insulin secretion promoter.

EXAMPLE 4
Production of 2'-fucosyllactose-comprising Cake

Cookies (30 pieces) were produced from the following blend.

| | |
|---|---|
| Cake flour | 100 g |
| Starch | 74 g |
| Water | 14 g |
| 2'-Fucosyllactose | 30 g |
| Baking powder | 2 teaspoons |
| Salt | 2 teaspoons |
| Egg | one egg |
| Butter | 80 g |
| Milk | 2 tablespoons |

EXAMPLE 5
Production of N-acetylneuraminic Acid-comprising Cake

Cookies (30 pieces) were produced from the following blend.

| | |
|---|---|
| Cake flour | 100 g |
| Starch | 74 g |
| Water | 14 g |
| N-Acetylneuraminic acid | 30 g |
| Baking powder | 2 teaspoons |
| Salt | 2 teaspoons |
| Egg | one egg |
| Butter | 80 g |
| Milk | 2 tablespoons |

EXAMPLE 6
Production of 2'-fucosyllactose-comprising Modified Powder Milk

The modified powder milk for infants of the following composition was produced.

| | |
|---|---|
| 2'-Fucosyllactose | 20 g |
| Skim milk | 5.04 kg |
| Whey protein concentrate | 158 g |

| -continued | |
|---|---|
| Lactose | 924 g |
| Water-soluble vitamin mixture | 75 g |
| Minerals | 75 g |
| Lipophilic vitamin | 578 g |

These components and homogenized together, sterilized by a routine method, concentrated and dried, to produce a modified milk.

Test Example 1
Activity of 2'-fucosyllactose to Promote Insulin Secretion (1)

Male 9-week-old C57BL/KsJ-db/db Jcl (abbreviated as "db/db" hereinafter) mice (Clea Japan, Inc.), which are model animals of Type II diabetes mellitus, were divided in groups each consisting of 6 mice, and fed a commercially available feed CE-2 (Clea Japan, Inc.) for one week, so as to accustom the animals to the environment.

After acclimation, an aqueous 10% solution of 2'-fucosyllactose (sometimes abbreviated as "2'-FL" hereinafter) was orally administered to the mice at 200 mg (2'-FL)/kg body weight in the morning and at 300 mg (2'-FL) /kg body weight in the evening. The same volume of Saline was administered to the control group. The aqueous 2'-FL solution and the saline were both dosed daily to the mice for 7 days.

During the dosing period, CE-2 was given together with drinking water ad libitum.

After 18-hour starvation from the final dosing on day 7, an aqueous 40% glucose solution was orally administered to 2 g (glucose)/kg body weight to the mice, to perform glucose tolerance test. Zero minute and 30 minutes after glucose loading, blood was taken from tail vein. 120 minutes thereafter, the mice were anesthetized with sodium pentobarbital at 50 mg/kg body weight, to collect the whole blood from inferior vena cava. Blood was centrifuged (4° C., 10000 rpm, 10 minutes), to obtain serum.

Insulin in the serum recovered was assayed by enzyme immunoassay using Lebis Insulin kit (for rats-T) (Shibayagi, Co., Ltd.) as follows. The kit reacts with insulin in the sera of both rats and mice.

First, the serum recovered was diluted with the buffer attached to the kit to 5 fold. 10 µl of the diluted serum was taken and divided in the wells of the antibody-immobilized plate into which 100 µl of a biotin-bound anti-insulin antibody was added, for reaction at ambient temperature for 2 hours. After the reaction, the plate was rinsed four times with the rinse solution attached to the kit. After rinsing, 100 µl of the peroxidase-avidin bound material was divided in the wells, for reaction at ambient temperature for 30 minutes. After reaction, the plate was rinsed four times with the rinse solution. After rinsing, 100 µl of the chromogenic solution was divided in the wells, for chromogenic reaction for 30 minutes, followed by addition of 100 µl of the reaction termination solution to each well. The absorbance of the reaction solution in the wells at 450 nm was read with a plate reader.

Herein, a standard curve was prepared by using the 200 ng/ml standard insulin solution (rat) attached to the kit as a standard solution to dilute the standard solution appropriately with the buffer solution attached to the kit for the same reaction as for the serum, and plotting the relation between the concentration and the absorbance (450 nm).

Based on the prepared standard curve and the absorbance from the reaction with the serum, the insulin concentration in the serum was determined. The results are shown in Table 1.

TABLE 1

Serum insulin concentration after glucose loading

| Groups | N | Insulin concentration (ng/ml) | | |
|---|---|---|---|---|
| | | Zero minute | 30 minutes | 120 minutes |
| Control group | 6 | 5.4 ± 1.7 | 4.8 ± 2.5 | 12.6 ± 6.0 |
| 2'-FL group | 6 | 6.7 ± 3.3 | 8.3 ± 3.9 | 26.1 ± 12.8 |

The numerical figure of the insulin concentration is shown in (mean ± standard deviation).

Table 1 shows that the insulin concentration after glucose loading in the db/db mice was increased via the continuous daily oral dosing of 2'-FL with the elapse of time, compared with the control group, indicating that insulin secretion was promoted.

Test Example 2
Activity of 2'-fucosyllactose to Promote Insulin Secretion (2)

Eleven male 9-week-old ICR mice as normal mice (SLC, Inc.) were fed a commercially available CE-2 (Clea Japan, Inc.) for one week, so as to accustom the mice to the environment.

After acclimation, an aqueous 10% solution of 2'-fucosyllactose was orally administered to the mice at 200 mg (2'-FL)/kg body weight in the morning and at 300 mg (2'-FL)/kg body weight in the evening. The same volume of saline was administered to the control group. The aqueous 2'-FL solution and saline were both dosed daily to the mice for 7 days.

During the dosing period, CE-2 was given together with drinking water ad libitum.

After 18-hour starvation from the final dosing on day 7, an aqueous 40% glucose solution was orally administered to 2 g (glucose)/kg body weight to the mice, to perform glucose tolerance test. Zero minute after glucose loading, blood was taken from a tail vein. 120 minutes thereafter, additionally, the mice were anesthetized with sodium pentobarbital at 50 mg/kg body weight, to draw the whole blood from inferior vena cava. Blood was centrifuged (4° C., 10000 rpm, 10 minutes), to obtain serum.

Insulin in the serum recovered was assayed by enzyme immunoassay using Lebis Insulin kit (for mice-T) (Shibayagi, Co., Ltd.). 10 µl of the serum was taken and divided in the wells of the antibody-immobilized plate into which 100 µl of a biotin-bound anti-insulin antibody was added, for reaction at ambient temperature for 2 hours. After the reaction, the plate was rinsed four times with the rinse solution attached to the kit. After rinsing, 100 µl of the peroxidase-avidin bound material was divided in the wells, for reaction at ambient temperature for 30 minutes.

After the reaction, the plate was rinsed four times with the rinse solution. After rinsing, 100 µl of the chromogenic solution was divided in the wells, for chromogenic reaction for 30 minutes, followed by addition of 100 µl of the reaction termination solution to each well. The absorbance of the reaction solution in the wells at 450 nm was read with a plate reader. Herein, a standard curve was prepared by using the standard insulin solution (mice, 200 ng/ml) attached to the kit as a standard solution to dilute the standard solution appropriately with the buffer solution attached to the kit for the same reaction as for the serum, and plotting the relation between the concentration and the absorbance (450 nm). Based on the prepared standard curve and the absorbance from the reaction with the serum, the insulin concentration in the serum was determined. The results are shown in Table 2.

TABLE 2

Serum insulin concentration after glucose loading

| Groups | N | Insulin concentration (ng/ml) | |
|---|---|---|---|
| | | Zero minute | 120 minutes |
| Control group | 5 | ND | 0.27 ± 0.13 |
| 2'-FL group | 6 | ND | 0.35 ± 0.24 |

The numerical figure of the insulin concentration is shown in (mean ± standard deviation).
ND means no insulin detection.

Table 2 shows that the insulin concentration 120 minutes after glucose loading in the ICR mice was increased via the continuous daily oral dosing of 2'-FL, compared with the control group, indicating that insulin secretion was promoted.

Test Example 3
Actions of Various Saccharides to Promote Insulin Secretion (1)

Group of male 9-week-old db/db mice (Clea Japan, Inc.) each consisting of 6 mice were fed CE-2 (Clea Japan, Inc.) for one week, so as to accustom the animals to the environment.

After acclimation, individual aqueous 10% solutions of globotriose (abbreviated "globo" hereinafter), N-acetyllactosamine (abbreviated as "LacNac" hereinafter) and N-acetylneuraminic acid (abbreviated as "NeuAc" hereinafter) were orally administered to the mice at 200 mg (saccharide)/kg body weight in the morning and at 300 mg (saccharide)/kg body weight in the evening.

The same volume of saline was administered to the control group. The individual aqueous saccharide solutions and saline were both dosed daily to the mice for 7 days. During the dosing period, CE-2 was given together with drinking water ad libitum.

On day 8, the whole blood was collected from the inferior vena cava of the mice under anesthesia with sodium pentobarbital at 50 mg/kg body weight. Blood was centrifuged (4° C., 10000 rpm, 10 minutes), to obtain serum.

Insulin in the serum recovered was assayed by enzyme immunoassay using Lebis Insulin kit (for rats-T) (Shibayagi, Co., Ltd.) in the same manner as in the Test Example 1.The results are shown in Table 3.

TABLE 3

Serum insulin concentration after dosing of the individual saccharides

| Groups | N | Insulin concentration (ng/ml) |
|---|---|---|
| Control group | 6 | 12.4 ± 5.9 |
| Globo group | 6 | 23.7 ± 16.4 |
| LacNac group | 6 | 26.8 ± 11.5 |
| NeuAc group | 6 | 68.4 ± 45.9 |

TABLE 3-continued

Serum insulin concentration after dosing of the individual saccharides

| Groups | N | Insulin concentration (ng/ml) |
|---|---|---|

The numerical figure of the insulin concentration is shown in (mean ± standard deviation).

Table 3 shows that the serum insulin concentration in the db/db mice was increased via the continuous daily oral dosing of globo, LacNac or NeuAc, compared with the control group, indicating that insulin secretion was promoted.

Test Example 4
Actions of Various Saccharides to Promote Insulin Secretion (2)

Groups of male 9-week-old db/db mice (Clea Japan, Inc.) each consisting of 6 mice were fed CE-2 (Clea Japan, Inc.) for one week, so as to accustom the animals to the environment.

After acclimation, individual aqueous 10% solutions of 3'-sialyllactose (abbreviated as "3'-SL" hereinafter), 6'-sialyllactose (abbreviated as "6'-SL") and 2'-FL were orally administered to the mice at 200 mg (saccharide)/kg body weight in the morning and at 300 mg (saccharide)/kg body weight in the evening. The both volume of saline was administered to the control group. The individual aqueous saccharide solutions and saline were both dosed daily to the mice for 7 days. During the dosing period, CE-2 was given together with drinking water ad libitum.

After 18-hour starvation from the final dosing on day 7, an aqueous 40% glucose solution was orally administered to 2 g (glucose)/kg body weight to the mice, to perform glucose tolerance test. Zero minute and 30 minutes after glucose loading, blood was taken from a tail vein. 120 minutes thereafter, further, the mice were anesthetized with sodium pentobarbital at 50 mg/kg body weight, to collect the whole blood from inferior vena cava. Blood was centrifuged (4° C., 10000 rpm, 10 minutes), to obtain serum.

Insulin in the serum recovered was assayed by enzyme immunoassay using Lebis Insulin kit (for rats-T) (Shibayagi, Co., Ltd.) in the same manner as in the Test Example 1. The results are shown in Table 4.

TABLE 4

Serum insulin concentration after glucose loading

| | | Insulin concentration (ng/ml) | | |
|---|---|---|---|---|
| Groups | N | Zero minute | 30 minutes | 120 minutes |
| Control group | 6 | 5.4 ± 1.7 | 4.8 ± 2.5 | 12.6 ± 6.0 |
| 3'-SL group | 6 | 6.0 ± 2.2 | 5.1 ± 1.9 | 22.0 ± 12.5 |
| 6'-SL group | 6 | 5.9 ± 3.0 | 6.6 ± 3.4 | 17.9 ± 6.3 |
| 2'-FL group | 6 | 6.7 ± 3.3 | 8.3 ± 3.9 | 26.1 ± 12.9 |

The numerical figure of the insulin concentration is shown in (mean ± standard deviation).

Table 4 shows that the serum insulin concentration during glucose loading in the db/db mice was increased via the continuous daily oral dosing of 3'-SL, 6'-SL or 2'-FL, compared with the control group, indicating that insulin secretion was promoted.

Test Example 5
Activity of Various Saccharides to Promote Insulin Secretion (3)

Groups of male 9-week-old db/db mice (Clea Japan, Inc.) each consisting of 6 mice were fed CE-2 (Clea Japan, Inc.) for one week, so as to accustom the animals to the environment.

After acclimation, individual aqueous 10% solutions of lacto-N-neotetraose (abbreviated as "LNnT" hereinafter) and NeuAc were orally administered to the mice at 200 mg (saccharide)/kg body weight in the morning and at 300 mg (saccharide)/kg body weight in the evening. The same volume of saline was administered to the control group. The individual aqueous saccharide solutions and saline were both dosed daily to the mice for 7 days. During the dosing period, CE-2 was given together with drinking water ad libitum.

After 18-hour starvation from the final dosing on day 7, an aqueous 40% glucose solution was orally administered to 2 g (glucose)/kg body weight to the mice, to perform glucose tolerance test. Zero minute and 30 minutes after glucose loading, blood was taken from a tail vein. 120 minutes thereafter, further, the mice was anesthetized with sodium pentobarbital at 50 mg/kg body weight, to collect the whole blood from inferior vena cava. Blood was centrifuged (4° C., 10000 rpm, 10 minutes), to obtain serum.

Insulin in the serum recovered was assayed by enzyme immunoassay using Lebis Insulin kit (for rats-T) (Shibayagi, Co., Ltd.) in the same manner as in the Test Example 1. The results are shown in Table 5.

TABLE 5

Serum insulin concentration after glucose loading

| | | Insulin concentration (ng/ml) | | |
|---|---|---|---|---|
| Groups | N | Zero minute | 30 minutes | 120 minutes |
| Control group | 6 | 11.2 ± 7.8 | 10.6 ± 3.7 | 17.4 ± 10.2 |
| LNnT group | 6 | 8.9 ± 2.0 | 21.7 ± 13.8 | 25.9 ± 13.2 |
| NeuAc group | 6 | 8.9 ± 7.7 | 18.5 ± 8.5 | 30.3 ± 10.7 |

The numerical figure of the insulin concentration is shown in (mean ± standard deviation).

Table 5 shows that the insulin concentration during glucose loading in the db/db mice was increased via the continuous daily oral dosing of LNnT or NeuAc, compared with the control group, indicating that insulin secretion was promoted.

Test Example 6
Activity of Various Saccharides to Promote Insulin Secretion in Blood and Activity Thereof to Suppress the Elevation of Blood Glucose Level Groups of male 9-week-old ICR mice (Japan SLC, Inc.) each consisting of 7 mice were fed CE-2 (Clea Japan, Inc.) for one week, so as to accustom the animals to the environment. Then, the mice were fasted for 18 hours.

An aqueous 10% solution of 2'-FL or NeuAc was intravenously administered to the mice to 500 mg (saccharide)/kg body weight, while an aqueous 40% glucose solution was orally administered simultaneously to 2 g (glucose)/kg body weight, to the mice. To the control group, physiological saline was administered intravenously, while glucose was orally administered simultaneously to 2 g/kg body weight. Zero minute and 30 minutes after glucose loading, blood was taken from a tail vein. 120 minutes thereafter, the mice were anesthetized with sodium pentobarbital at 50 mg/kg body weight, to collect the whole blood from inferior vena cava. Blood was centrifuged (4° C., 10000 rpm, 10 minutes), to obtain serum.

Insulin in the serum recovered was assayed by enzyme immunoassay using Lebis Insulin kit (for mice-T) (Shibayagi, Co., Ltd.) in the same manner as in the Test Example 2.

Furthermore, the glucose concentration in the serum recovered was also assayed. The glucose concentration was assayed, using Glucose CII-TEST WAKO (WAKO Pure Chemical Industries, Ltd.). 2 µl of the recovered serum was placed in a 96-well plate, followed by addition of 200 µl of the chromogenic solution attached to the kit, for incubation at 37° C. for 10 minutes. After incubation, the absorbance at 490 nm was assayed with a plate reader. Herein, a standard curve was prepared by using aqueous 500 mg/dl glucose solution as the standard solution to dilute the standard solution appropriately for the same reaction as for the serum, and plotting the relation between the concentration and the absorbance (490 nm). Based on the prepared standard curve and the absorbance from the reaction with the serum, the glucose concentration in the serum was determined.

The serum insulin concentration and the serum glucose concentration are shown in Table 6 and Table 7, respectively.

TABLE 6

Serum insulin concentration after glucose loading

| | | Insulin concentration (pg/ml) | | |
|---|---|---|---|---|
| Groups | N | Zero minute | 30 minutes | 120 minutes |
| Control group | 7 | ND | 161.3 ± 67.9 | 258.6 ± 308.9 |
| 2'-FL group | 7 | ND | 192.3 ± 57.4 | 2090.7 ± 533.1 |
| NeuAc group | 7 | ND | 178.3 ± 105.5 | 384.4 ± 394.1 |

The numerical figure of the insulin concentration is shown in (mean ± standard deviation).
ND means no detection.

TABLE 7

Serum glucose concentration after glucose loading

| | | Glucose concentration (mg/dl) | | |
|---|---|---|---|---|
| Groups | N | Zero minute | 30 minutes | 120 minutes |
| Control group | 7 | 109.7 ± 17.9 | 377.2 ± 107.2 | 240.2 ± 50.7 |
| 2'-FL group | 7 | 102.4 ± 23.3 | 331.4 ± 68.6 | 169.2 ± 29.5 |
| NeuAc group | 7 | 102.6 ± 12.1 | 300.9 ± 101.6 | 197.6 ± 28.8 |

The numerical figure of the insulin concentration is shown in (mean ± standard deviation).

Table 6 and Table 7 show that the serum insulin concentration after glucose loading in the ICR mice was increased via the intravenous dosing of 2'-FL or NeuAc, compared with the control group, indicating that insulin secretion was promoted and that the increase of the serum glucose concentration was suppressed as the insulin concentration increased, compared with the control group, indicating that the elevation of the blood glucose level was suppressed.

Test Example 7
Activity of 2'-fucosyllactose to Promote Insulin Secretion (3)

Groups of male 9-week-old ICR mice (Japan SLC, Inc.) each consisting of 7 mice were fed a commercially available CE-2 (Clea Japan, Inc.) for one week, so as to accustom the mice to the environment. Thereafter, an aqueous 1% solution of 2'-FL was intravenously administered to the mice to 50 mg (2'-FL)/kg body weight. The same volume of saline was administered to the control group. Zero minute and 30 minutes after dosing, blood was taken from a tail vein. 120 minutes thereafter, the mice was anesthetized with sodium pentobarbital at 50 mg/kg body weight, to collect the whole blood from inferior vena cava. Blood was centrifuged (4° C., 10000 rpm, 10 minutes), to obtain serum.

Insulin in the serum recovered was assayed by enzyme immunoassay using Lebis Insulin kit (for mice-T) (Shibayagi, Co., Ltd.) in the same manner as in the Test Example 2. The results are shown in Table 8.

TABLE 8

Serum insulin concentration after 2'-FL dosing

| | | Insulin concentration (pg/ml) | | |
|---|---|---|---|---|
| Groups | N | Zero minute | 30 minutes | 120 minutes |
| Control group | 7 | ND | ND | ND |
| 2'-FL group | 7 | ND | 168.6 ± 40.2 | 2035.9 ± 1098.0 |

The numerical figure of the insulin concentration is shown in (mean ± standard deviation).
ND means no detection.

Table 8 shows that the serum insulin concentration in the ICR mice was increased via the intravenous 2'-FL dosing, compared with the control group, indicating that insulin secretion was promoted.

Test Example 8
Actions of 2'-fucosyllactose to Promote Insulin Secretion and to Suppress the Elevation of Blood Glucose Level Groups of male 8-week-old ICR mice (Japan SLC, Inc.) each consisting of 6 mice were fed CE-2 (Clea Japan, Inc.) for one week, so as to accustom the animals to the environment.

Then, the mice accustomed were fasted for 18 hours. An aqueous 2% solution of 2'-FL was orally administered to the mice to 100 mg (2'-FL)/kg body weight, while 0.9% saline was administered orally to the control group. Two hours after the 2'-FL dosing, an aqueous 40% glucose solution was orally administered to 2 g (glucose)/kg body weight to the mice, for glucose tolerance test. Zero minute, 30 minutes and 120 minutes after glucose loading, blood was taken from a tail vein. Blood glucose was assayed with a simple-type blood glucose assay apparatus Medisafe Reader GR-101 (Terumo, Co., Ltd.), while the serum was collected.

Insulin in the serum recovered was assayed by enzyme immunoassay using Morinaga ultra-sensitive rat insulin assay kit (Morinaga Biochemical Research Institute, Co., Ltd.) described below. 15 µl of the serum was divided in the wells of an antibody-immobilized plate, where 85 µl of the diluent attached to the kit was divided therein, for reaction at 4° C. for 2 hours. After the reaction, the plate was rinsed five times with the rinse solution attached to the kit. After rinsing, 100 µl of an enzyme-labeled guinea pig anti-rat insulin antibody was divided in each well, for reaction at ambient temperature for 30 minutes. After the reaction, the plate was rinsed seven times with the rinse solution. After rinsing, 100 μl of the enzyme substrate solution was divided in the wells, for chromogenic reaction for 30 minutes, followed by addition of 100 μl of the reaction termination solution to each well. The absorbance of each well at 450 nm (principal wave length) and 655 nm (sub wave length) was measured with BioRad Model 3550 microplate reader (BioRad Laboratories, Inc.). Additionally, a standard curve was prepared by diluting 2 ng of the standard insulin (mouse) attached to the kit with 100 μl of saline to use the resulting 20 ng/ml insulin solution as the standard solution, diluting the standard solution appropriately with the diluent attached to the kit for the same reaction as for the serum, and plotting the relation between the concentration and the absorbance at the principal wave length of 450 nm and at the sub wave length of 655 nm. Based on the prepared standard curve, the serum insulin concentration corresponding to the absorbance during the reaction with the serum was determined. The results are shown in Tables 9 and 10.

TABLE 9

Serum blood glucose level after glucose loading

| Groups | N | Blood glucose level (mg/ml) | | | |
|---|---|---|---|---|---|
| | | −120 minutes | 0 minute | 60 minutes | 120 minutes |
| Control group | 6 | 123.3 ± 25.4 | 118.2 ± 14.8 | 251.0 ± 53.8 | 159.5 ± 18.7 |
| 2'-FL group | 6 | 131.4 ± 23.6 | 108.6 ± 4.4 | 218.9 ± 29.0 | 147.3 ± 14.2 |

Blood glucose is shown in (mean ± standard deviation).

TABLE 10

Serum insulin concentration 60 minutes after glucose loading

| Groups | N | Insulin concentration (pg/ml) |
|---|---|---|
| Control group | 6 | 26.4 ± 33.4 |
| 2'-FL group | 6 | 82.6 ± 91.7 |

The numerical figure of the insulin concentration is shown in (mean ± standard deviation).

Table 9 and Table 10 show that the serum insulin concentration 60 minutes after glucose loading in the ICR mice was increased via the single oral dosing of 2'-FL 120 minutes before glucose dosing, compared with the control group, indicating that insulin secretion was promoted and that the elevation of blood glucose level was suppressed.

Test Example 9
Activity of 2'-fucosyllactose to Promote Insulin Secretion in Type I Diabetes Mellitus Model Animal Male 7-week-old Wistar rats (Japan SLC, Inc.) were fed CE-2 (Clea Japan, Inc.) for one week, so as to accustom the rats to the environment.

After 18-hour starvation of the accustomed rats, 300 ml of 50 mM citrate buffer, pH 4.5 containing 15 mg of streptozotocin (WAKO Pure Chemical Industries, Inc.; abbreviated as "STZ" hereinafter) was prepared and administered to 25 mg (STZ)/kg body weight from their tail vein. Five days after the STZ administration, the rats were fasted for 18 hours. Blood was taken from puncture in the tail vein to assay blood glucose with a simple-type blood glucose assay apparatus Medisafe Reader GR-101 (Terumo, Co., Ltd.), to select 5 rats (Nos. 1, 3, 4, 5, 8) at mild state of diabetes mellitus with a blood glucose level of 200 mg/dl or less.

An aqueous 2% solution of 2'-fucosyllactose was prepared and administered to the rat No. 1 from the tail vein to 50 mg/kg body weight on a 2'-FL dose basis. 0.9% physiological saline was administered to rats Nos. 3, 4, 5 and 8. Two hours after 2'-FL dosing, an aqueous 40% glucose solution was orally administered to 1 g/kg body weight to the rats for glucose tolerance test. Zero minute and 30, 60, 120, and 240 minutes after glucose loading, blood was taken from a tail vein, to assay blood glucose with Medisafe Reader GR-101 and collect the serum.

12 days after the STZ dosing, the rats were fasted for 18 hours. An aqueous 2% solution of 2'-FL at 50 mg (2'-FL)/kg body weight was administered to rats Nos. 3, 4, 5 and 8 on a 2'-FL dose basis through their tail veins. To the rat No. 1 was administered 0.9% physiological saline. Two hours after 2'-FL dosing, an aqueous 40% glucose solution was orally administered to 1 g (glucose)/kg body weight to the rats, for glucose tolerance test. Zero minute and 30, 60, 120, and 240 minutes after glucose loading, blood was taken from a tail vein, to assay blood glucose with Medisafe Reader GR-101 and collect the serum.

Insulin in the serum was assayed by enzyme immunoassay using Morinaga ultra-sensitive rat insulin assay kit (Morinaga Biochemical Research Institute, Co., Ltd.) in the same manner as in Test Example 8. Additionally, a standard curve was prepared by diluting 2.56 ng of the standard insulin (rat) attached to the kit with 100 μl of saline to use the resulting 25.6 ng/ml insulin solution as the standard solution, diluting the standard solution appropriately with the diluent attached to the kit for the same reaction as for the serum, and plotting the relation between the concentration and the absorbance at the principal wave length of 450 nm and at the sub wave length of 655 nm. Based on the prepared standard curve, serum insulin corresponding to the absorbance during the reaction with the serum was determined. The results are shown in Tables 11 and 12.

TABLE 11

Serum insulin concentration

| Rat Nos. | Dosed substance | Serum insulin concentration (pg/ml) | |
|---|---|---|---|
| | | 0 minute | 30 minutes |
| 1 | Saline | 10.2 | 43.1 |
| | 2'-FL | 180.4 | 475.5 |
| 3 | Saline | 57.0 | 120.8 |
| | 2'-FL | 312.5 | 148.4 |
| 4 | Saline | 148.4 | 98.7 |
| | 2'-FL | 125.8 | 331.1 |
| 5 | Saline | 81.9 | 86.7 |
| | 2'-FL | 697.0 | 586.6 |
| 8 | Saline | 229.4 | 329.7 |
| | 2'-FL | 197.4 | 915.1 |

TABLE 12

Blood glucose level after glucose loading

| Rat Nos. | Dosed substance | Blood glucose level (mg/dl) | | | | | |
|---|---|---|---|---|---|---|---|
| | | −120 minutes | 0 minute | 30 minutes | 60 minutes | 120 minutes | 240 minutes |
| 1 | Saline | 120 | 110 | 195 | 278 | 254 | 176 |
| | 2'-FL | 117 | 138 | 152 | 158 | 136 | 50 |
| 3 | Saline | 120 | 175 | 276 | 315 | 325 | 277 |
| | 2'-FL | 108 | 135 | 167 | 172 | 181 | 146 |

TABLE 12-continued

Blood glucose level after glucose loading

| Rat Nos. | Dosed sub-stance | Blood glucose level (mg/dl) | | | | | |
|---|---|---|---|---|---|---|---|
| | | −120 minutes | 0 minute | 30 minutes | 60 minutes | 120 minutes | 240 minutes |
| 4 | Saline | 167 | 168 | 245 | 285 | 348 | 310 |
|   | 2'-FL  | 197 | 186 | 273 | 355 | 342 | 328 |
| 5 | Saline | 115 | 119 | 215 | 220 | 158 | 112 |
|   | 2'-FL  | 122 | 97  | 237 | 253 | 224 | 139 |
| 8 | Saline | 117 | 116 | 198 | 275 | 249 | 185 |
|   | 2'-FL  | 121 | 134 | 162 | 154 | 161 | 139 |

Table 11 and Table 12 show that the serum insulin concentration was increased via glucose loading 2 hours after the intravenous dosing of 2'-FL to the STZ-induced diabetic rats, indicating that insulin secretion was promoted and that the increase of blood glucose level was suppressed.

What is claimed is:

1. A method for promoting insulin secretion, comprising administering an effective amount of at least one member selected from the group consisting of a N-acetyllactosamine, lacto-N-neotetraose, globotriose, 2'-fucosyllactose, 3'-sialyllactose, 6'-sialyllactose, and N-acetylneuraminic acid, to a patient with Type II diabetes mellitus.

2. The method for promoting insulin secretion according to claim 1, where the patient is a human.

3. The method for promoting insulin secretion according to claim 1, where the patient is an animal.

4. The method for promoting insulin secretion according to claim 3, where the animal is a domestic mammal, domestic fowl, or cultivated fish.

5. The method for promoting insulin secretion according to any one of claims 1 or 2 to 4, where the administration is carried out orally.

6. The method for promoting insulin secretion according to any of one claims 1 or 2 to 4, where the administration is carried out by injection.

7. A method for suppressing the elevation of a blood glucose level, comprising administering an effective amount of at least one member selected from the group consisting of N-acetyllactosamine, lacto-N-neotetraose, globotriose, 2'-fucosyllactose, 3'-sialyllactose, 6'-sialyllactose, and N-acetylneuraminic acid, to a patient with Type II diaebetes mellitus.

8. The method for suppressing the elevation of a blood glucose level according to claim 7, where the patient is a human.

9. The method for suppressing the elevation of a blood glucose level according to claim 7, where the patient is an animal.

10. The method for suppressing the elevation of a blood glucose level according to claim 9, where the animal is a domestic mammal, domestic fowl, or cultivated fish.

11. The method for suppressing the elevation of a blood glucose level according to any one of claims 7 or 8 to 10, where the administration is carried out orally.

12. The method for suppressing the elevation of a blood glucose level according to any one of claims 7 or 8 to 10, where the administration is carried out by injection.

13. A method for ameliorating diabetes mellitus, comprising administering an effective amount of at least one member selected from the group consisting of N-acetyllactosamine, lacto-N-neotetraose, globotriose, 2'-fucosyllactose, 3'-sialyllactose, 6'-sialyllactose, and N-acetylneuraminic acid, to a patient with Type II diabetes mellitus.

14. The method for ameliorating diabetes mellitus according to claim 13, where the patient is a human.

15. The method for ameliorating diabetes mellitus according to claim 13, where the patient is an animal.

16. The method for ameliorating diabetes mellitus according to claim 15, where the animal is a domestic mammal, domestic fowl, or cultivated fish.

17. The method for ameliorating diabetes mellitus according to any one of claims 13 or 14 to 16, where the administration is carried out orally.

18. The method for ameliorating diabetes mellitus according to any one of claims 13 or 14 to 16, where the administration is carried out by injection.

* * * * *

UNITED STATES PATENT AND TRADEMARK OFFICE
CERTIFICATE OF CORRECTION

PATENT NO. : 6,946,451 B2
DATED : September 20, 2005
INVENTOR(S) : Miho Takada et al.

It is certified that error appears in the above-identified patent and that said Letters Patent is hereby corrected as shown below:

Column 1,
Line 54, "under which such food" should read -- by which such foods --.

Column 2,
Line 35, "claim 1," should read -- (1), --;
Line 39, "claim 2," should read -- (2), --;
Line 44, "claim 1," should read -- (1), --; and
Line 49, "claims 1 to 4," should read -- (1) to (4), --.

Column 4,
Line 38, "(38)" should read -- ¶ (38) --; and
Line 45, "prosong" should read -- prising --.

Column 6,
Line 2, "Sosceity," should read -- Society, --;
Line 15, "or comestible acceptable" should read -- acceptable or comestible --; and
Line 48, "sucrose," should be deleted (repetition).

Column 7,
Line 3, "dose" should be deleted; and
Line 4, "promoter," should read -- promoters, --.

Column 8,
Line 30, "milks" should read -- milks, --;
Line 31, "pulverized" should read -- pulverized, --; and "include" should read -- includes --; and
Line 45, "αs-casein," should read -- α-casein --.

Column 12,
Line 4, "acidifier" should read -- acidifiers --.

Column 14,
Line 26, "Saline" should read -- saline --.

Column 17,
Line 28, "both volume" should read -- same volume --.

Column 18,
Line 23, "was" should read -- were --.

UNITED STATES PATENT AND TRADEMARK OFFICE
CERTIFICATE OF CORRECTION

PATENT NO.    : 6,946,451 B2
DATED         : September 20, 2005
INVENTOR(S)   : Miho Takada et al.

It is certified that error appears in the above-identified patent and that said Letters Patent is hereby corrected as shown below:

Column 23,
Lines 35 and 38, "claims 1 or 2 to 4," should read -- claims 1 to 4, --.

Column 24,
Lines 15 and 18, "claims 7 or 8 to 10," should read -- claims 7 to 10, --; and
Lines 35 and 38, "claims 13 or 14 to 16," should read -- claims 13 to 16, --.

Signed and Sealed this

Seventh Day of February, 2006

JON W. DUDAS
*Director of the United States Patent and Trademark Office*